United States Patent [19]

Weber et al.

[11] E Re. 28,935

[45] Reissued Aug. 17, 1976

[54] 5-PHENYL-7-CHLORO-1H-1,5-BENZODIAZEPINE-2,4-(3H,5H)-DIONES

[75] Inventors: Karl-Heinz Weber, Gau-Algesheim; Karl Zelle; Peter Danneberg, both of Inglheim am Rheim; Rolf Glesemann, Bingen, all of Germany; Karl Heinz Hauptmann, deceased, late of Ingelheim am Rheim, Germany, by Maria Hauptman, heiress, Bonn, Germany

[73] Assignee: Boehringer Ingelheim GmbH, Ingelheim am Rhein, Germany

[22] Filed: June 17, 1975

[21] Appl. No.: 587,591

Related U.S. Patent Documents

Reissue of:

[64] Patent No.: 3,684,798
Issued: Aug. 15, 1972
Appl. No.: 111,716
Filed: Feb. 1, 1971

U.S. Applications:

[63] Continuation-in-part of Ser. No. 89,482, Nov. 13, 1970, abandoned, which is a continuation of Ser. No. 703,188, Feb. 5, 1968, abandoned.

[30] Foreign Application Priority Data

| | | |
|---|---|---|
| Feb. 7, 1967 | Germany | B 91071 |
| Jan. 18, 1968 | Germany | B 96281 |
| Jan. 18, 1968 | Germany | B 96282 |

[52] U.S. Cl. ..... 260/239.3 B; 424/244; 424/267

[51] Int. Cl.[2] ..... C07D 243/12

[58] Field of Search ..... 260/239.3 B

[56] References Cited

OTHER PUBLICATIONS

Buchi et al. "Helv. Chim. Acta" vol. 39, pp. 952–963 (1956).

*Primary Examiner*—Natalie Trousof
*Assistant Examiner*—Robert T. Bond
*Attorney, Agent, or Firm*—Hammond & Littell

[57] ABSTRACT

Compounds of the formula

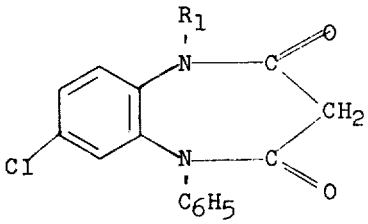

wherein $R_1$ is hydroxy-alkyl of 2 to 4 carbon atoms; haloalkyl of 2 to 4 carbon atoms; di(alkyl of 2 to 4 carbon atoms)amino-alkyl of 2 to 4 carbon atoms; γ-piperidino-propyl; alkoxy of 1 to 2 carbon atoms - alkyl of 1 to 4 carbon atoms; (alkoxy of 1 to 2 carbon atoms)carbonyl-alkyl of 1 to 4 carbon atoms; (alkyl of 1 to 2 carbon atoms)mercaptoalkyl of 1 to 4 carbon atoms; [ straight or branched alkenyl of 3 to 5 carbon atoms; ] (alkoxy of 1 to 2 carbon atoms)carbonyl-alkenyl of 2 to 4 carbon atoms; or halo-alkenyl of 2 to 4 carbon atoms;

the compounds are useful as psychosedatives and anticonvulsives.

8 Claims, No Drawings

5-PHENYL-7-CHLORO-1H-1,5-BENZODIAZEPINE-2,4-(3H,5H)-DIONES

Matter enclosed in heavy brackets [ ] appears in the original patent but forms no part of this reissue specification; matter printed in italics indicates the additions made by reissue.

This is a continuation-in-part of copending application Ser. No. 89,482, filed Nov. 13, 1970, *now abandoned*, which in turn is a continuation of application Ser. No. 703,188, filed Feb. 5, 1968, now abandoned.

This invention relates to novel 5-phenyl-7-chloro-1H-1,5-benzodiazepine-2,4-diones and methods of preparing these compounds.

More particularly, the present invention relates to compounds of the formula

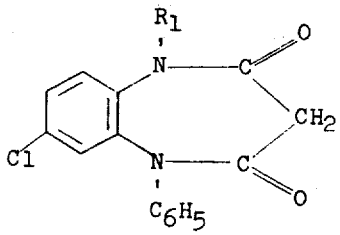

(I)

wherein $R_1$ is hydroxy-alkyl of 2 to 4 carbon atoms; haloalkyl of 2 to 4 carbon atoms; di(alkyl of 2 to 4 carbon atoms)amino-alkyl of 2 to 4 carbon atoms; γ-piperidino-propyl; alkoxy of 1 to 2 carbon atoms-alkyl of 1 to 4 carbon atoms; (alkoxy of 1 to 2 carbon atoms)carbonyl-alkyl of 1 to 4 carbon atoms; (alkyl of 1 to 2 carbon atoms)mercapto-alkyl of 1 to 4 carbon atoms; [ straight or branched alkenyl of 3 to 5 carbon atoms; ] (alkoxy of 1 to 2 carbon atoms)carbonyl-alkenyl of 2 to 4 carbon atoms.

The compounds according to the present invention may be prepared by a number of different methods involving well known chemical principles, among which the following have proved to be particularly convenient and efficient:

Method A

By cyclizing an N-phenyl-N-phenyl-N-(2-amino-5-chloro-phenyl)-malonic acid lower alkyl ester amide of the formula

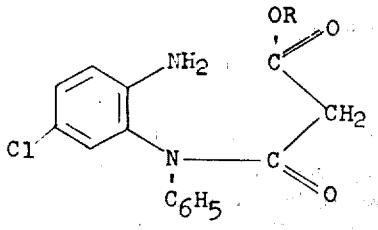

(II)

wherein R is lower alkyl, and subsequently alkylating the cyclization product in the 1-position.

Method B

By cyclizing a 2-amino-5-chloro-diphenyl-amine of the formula

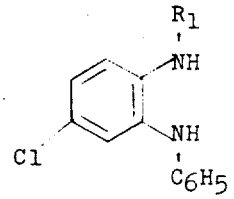

(III)

wherein $R_1$ has the same meanings as in formula I, with a malonic acid or alkylmalonic acid dihalide and, if necessary, alkylating the cyclization product thus obtained in the 1-position.

In method A the hydrolysis and ring closure proceed smoothly and with good yields in an acid as well as an alkaline medium, preferably in the presence of an alcoholic or aqueous alcoholic solvent; however, other inert solvents such as tetrahydrofuran or dioxane, are also suitable; for acid cyclization, acetonitrile may also be used as the solvent. Mineral acids, and particularly hydrohalic acids, such as hydrochloric acid, hydrobromic acid, hydroiodic acid, sulfuric acid, phosphoric acid and perchloric acid are preferably used as acid cyclization agents. Examples of alkaline cyclization agents are sodium alcoholates and alkali metal hydroxides.

The reaction periods depend upon the quantity of acid or alkali employed and upon the type of solvent used; they vary between several hours and several days. The preferred reaction temperatures are preferably between +20°C. and the boiling point of the solvent which is used.

The preparation of an end product of the formula I, wherein $R_1$ is unsubstituted or substituted alkyl, may be carried out in various ways. One may, for instance, start from a compound of formula I wherein $R_1$ is hydrogen and exchange the same for an alkyl group with the aid of a customary alkylating agent, such as an alkyl halide or an alkyl sulfate, such as a dialkylsulfate. For this purpose an alkali metal salt of a compound of formula I is dissolved or suspended in a suitable solvent, the alkylating agent is added to the solution or suspension, and the reaction mixture is heated. For the preparation of an end product of the formula I wherein $R_1$ is hydroxy-alkyl, a compound of the formula I wherein $R_1$ is hydrogen may be reacted with an alkyleneoxide in the presence of a strong base, such as Triton-B. If the cyclization is carried out under alkaline conditions, the alkylation of the 1-position may also be effected after the cyclization is finished, without prior isolation of the 1-unsubstituted benzodiazepine-2,4-dione cyclization product. In this case the alkylating agent is added to the cyclization reaction solution containing the cyclization product, and the mixture heated.

In method B the reaction is preferably carried out in the presence of a suitable inert organic solent, such as benzene, toluene, xylene, tetrahydrofuran, dioxan or dimethylformamide, at room temperature or, more advantageously, at the boiling point of the particular solvent which is used. In some cases the addition of a tertiary organic base, such as pyridine, has proved to have a favorable influence upon the course of the reaction. An end product of the formula I, wherein $R_1$ is hydrogen, may be subsequently alkylated, as described in conjunction with method A.

If, in a compound of the formula I, $R_1$ is hydroxy-alkyl, the hydroxyl group may subsequently be replaced by a halogen atom by treatment with a thionyl halide in the presence of dimethylformamide, or converted into an alkoxy group by treatment with a diazoalkane in the presence of borontrifluoride etherate.

If $R_1$ in a compound of the formula I is dialkylaminoalkyl, it is possible to introduce a double bond into the alkyl moiety by quaternization and splitting off trialkylamine.

[ Furthermore, in a compound of the general formula I, wherein $R_1$ is alkenyl, this substituent may be partially or completely hydrogenated by known methods. ]

The N-phenyl-N-(2-amino-5-chloro-phenyl)-malonic acid lower alkyl ester amides of the formula II used as starting materials for method A are also novel. They may be prepared by reacting a correspondingly substituted N-phenyl-N-2-nitro-5-chloro-phenyl)-amine with a malonic acid monoalkyl ester halide to obtain an N-phenyl-N-(2-nitro-5-chloro-phenyl)-malonic acid alkyl ester amide, and subsequently reducing the nitro group according to the following reaction sequence:

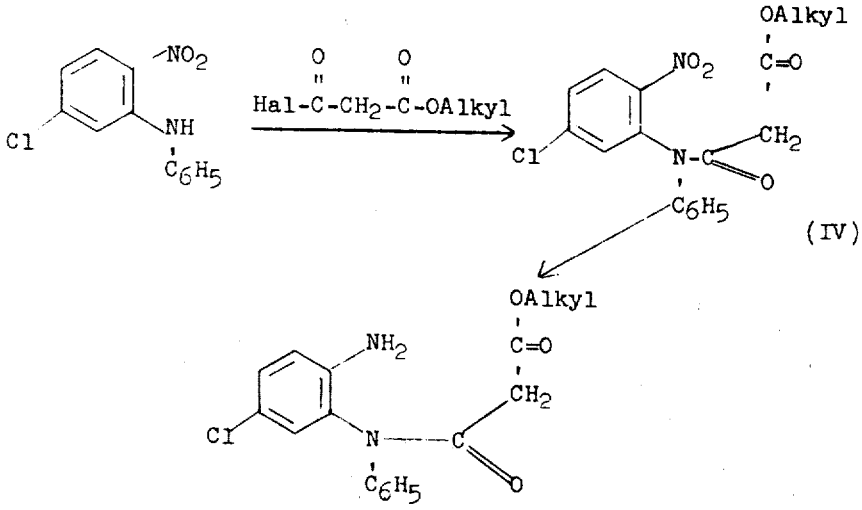

Thus, the preparation of an N-phenyl-N-(2-nitro-5-chloro-phenyl)-malonic acid alkyl ester amide of the formula IV is carried out, for example, by heating a solution of N-phenyl-N-(2-nitro-5-chloro-phenyl)-amine in a suitable solvent, such as benzene, toluene or xylene, with a malonic acid ester halide, whereby the nitro compound IV is always obtained with good yields (80%) and in crystalline form.

The subsequent reduction of compound IV may be effected by nascent or catalytic hydrogenation, for example, by hydrogenation with Raney-nickel or with a mixture of iron and glacial acetic acid.

For the cyclization to form the 5-phenyl-7-chloro-1H-1,5-benzodiazepine-2,4-dione end product of the formula I it is not absolutely necessary to start from an isolated compound of the formula II; instead, the solution containing the hydrogenated inermediate product II may directly be treated with the cyclization agents mentioned above, after removal of the catalyst.

The starting compounds of the formula III may be prepared by conventional methods, for example, by catalytic reduction of the corresponding 2-nitrodiphenylamine, or analogous to the method described in Chem. Berichte, Volume 34, page 4204 (1902), and Volume 37, page 552 (1904), that is, by cyclizing a 2-aminodiphenyl-amine with formic acid, alkylating at the nitrogen atom in the cyclization product by means of an alkyl iodide, and subsequently splitting the ring with an alkali.

The following examples further illustrate the present invention and will enable others skilled in the art to understand it more completely. It should be understood, however, that the invention is not limited solely to the particular examples given below.

EXAMPLE 1

1-(β-Hydroxy-ethyl)-5-phenyl-7-chloro-1H-1,5-benzodiazepine-2,4-(3H,5H)-dione by method A A mixture consisting of 28.6 gm (0.1 mol) of 5-phenyl-7-chloro-1H-1,5-benzodiazepine-2,4-(3H,5H)-dione, 500 ml of methanol, 25 ml of water, 10–15 ml of ethyleneoxide and 1 ml of Triton B (methanolic 35% solution of benzyl trimethylammonium hydroxide) was stirred at room temperature for about eight hours. Thereafter, the clear solution formed thereby was evaporated, the residue was taken up in methylene chloride, and the resulting solution was extracted with water, dried and evaporated. The residue was recrystallized from ethanol, yielding 25.6 gm (78% of theory) of the colorless crystalline compound of the formula

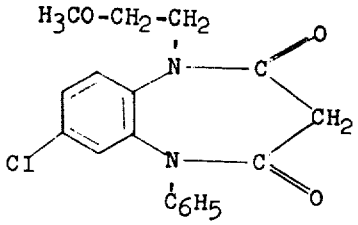

having a melting point of 208–210°C.

EXAMPLE 2

1-(β-Methoxy-ethyl)-5-phenyl-7-chloro-1H-1,5-benzodiazepine-2,4-(3H,5H)-dione by method A 28.6 gm (0.1 mol) of 5-phenyl-7-chloro-1H-1,5-benzodiazepine-2,4-(3H,5H)-dione were suspended in 750 ml of absolute tetrahydrofuran, 5 gm of a 50% dispersion of sodium hydride in tetrahydrofuran were added to the Suspension and the mixture was stirred for two hours at room temperature, whereby everything went into solution. 21–28 gm (0.15 – 0.2 mol) of β-bromoethyl methyl ether were then added to the solution, and the resulting mixture was refluxed for 15–20 hours. Thereafter, the reaction solution was evaporated in vacuo, residue was admixed with water, and the aqueous mixture was extracted with methylene chloride. The methylene chloride extract was vacuum-filtered to remove insoluble components, the filtrate was evaporated, and the residue was recrystallized from isopropyl ether, yielding 22 gm (64% of theory) of the compound of the formula

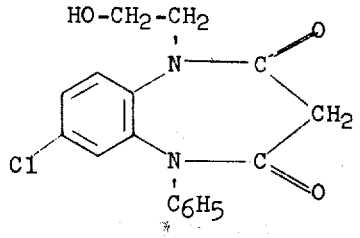

having a melting point of 178–180°C.

[EXAMPLE 3]

[Using a procedure analogous to that described in Example 2, 1-allyl-7-chloro-5-phenyl-1H-1,5-benzodiazepine-2,4-(3H,5H)-dione, m.p. 203–206°C, of the formula

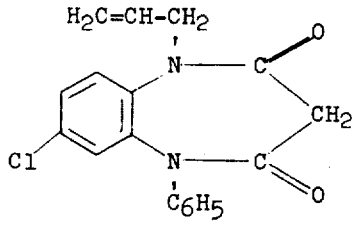

was prepared from 7-chloro-5-phenyl-1H-1,5-benzodiazepine-2,4-(3H,5H)-dione and allyl bromide.]

[EXAMPLE 4]

[Using a procedure analogous to that described in Example 2, 1-[isopenten-(4')-yl-1']-7-chloro-5-phenyl-1H-1,5-benzodiazepine-2,4-(3H,5H)-dione, m.p. 105–107°C, of the formula

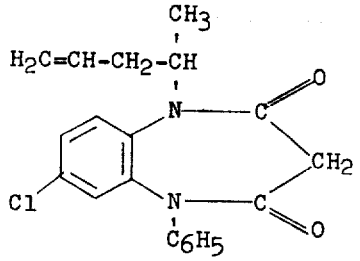

was prepared from 7-chloro-5-phenyl-1H-1,5-benzodiazepine-2,4-(3H,5H)-dione and isopenten-(4)-yl-1-bromide.]

[EXAMPLE 5]

[Using a procedure analogous to that described in Example 2, 1-dimethylallyl-7-chloro-5-phenyl-1H-1,5-benzodiazepine-2,4-(3H,5H)-dione, m.p. 154–156°C, of the formula

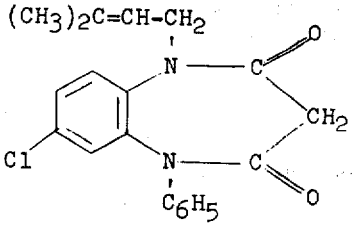

was prepared from 7-chloro-5-phenyl-1H-1,5-benzodiazepine-2,4-(3H,5H)-dione and dimethylallyl bromide.]

EXAMPLE [6] *3*

Using a procedure analogous to that described in Example 2, 1-chloroallyl-7-chloro-5-phenyl-1H-1,5-benzodiazepine-2,4-(3H,5H)-dione, m.p. 153–154°C, of the formula

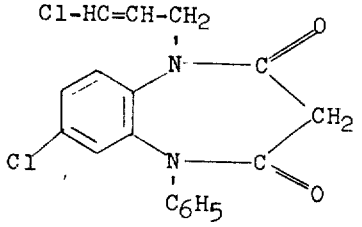

was prepared from 7-chloro-5-phenyl-1H-1,5-benzodiazepine-2,4-(3H,5H)-dione and chloroallyl bromide.

EXAMPLE [7] *4*

Using a procedure analogous to that described in Example 1, 1-(1'-hydroxy-propyl-2')-7-chloro- 5-phenyl-1H-1,5-benzodiazepine-2,4-(3H,5H)-dione, m.p. 192–194°C, of the formula

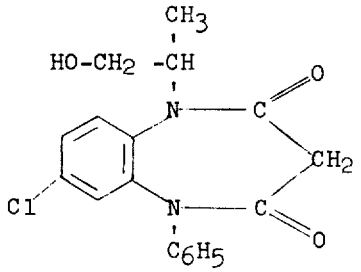

was prepared from 7-chloro-5-phenyl-1H-1,5-benzodiazepine-2,4-(3H,5H)-dione and propyleneoxide.

EXAMPLE [8] *5*

Using a procedure analogous to that described in Example 2, 1-(β-methoxy-ethyl)-7-chloro-5-phenyl-1H-1,5-benzodiazepine-2,4-(3H,5H)-dione, m.p. 175–178°C, of the formula

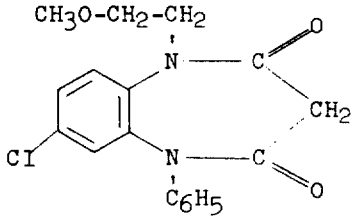

was prepared from 7-chloro-5-phenyl-1H-1,5-benzodiazepine-2,4-(3H,5H)-dione and β-methoxyethyl bromide.

EXAMPLE [9] *6*

Using a procedure analogous to that described in Example 2, 1-methoxymethyl-7-chloro-5-phenyl-1H-1,5-benzodiazepine-2,4-(3H,5H)-dione, m.p. 164–165°C, was prepared from 7-chloro- 5-phenyl-

1H-1,5-benzodiazepine-2,4-(3H,5H)-dione and methoxymethyl bromide.

EXAMPLE [10] 7

Using a procedure analogous to that described in Example 2, 1-(β-ethoxyethyl)-7-chloro-5-phenyl-1H-1,5-benzodiazepine-2,4-(3H,5H)-dione, m.p. 135–137°C, was prepared from 7-chloro-5-phenyl-1H-1,5-benzodiazepine-2,4-(3H,5H)-dione and β-ethoxyethyl bromide.

EXAMPLE [11] 8

Using a procedure analogous to that described in Example 1, 1-(β-dimethylamino-ethyl)-7-chloro-5-phenyl-1H-1,5-benzodiazepine-2,4-(3H,5H)-dione, m.p. 148–150°C, of the formula

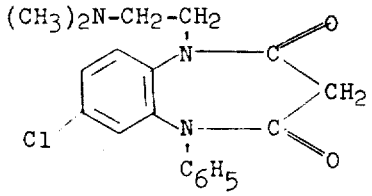

was prepared from 7-chloro-5-phenyl-1H-1,5-benzodiazepine-2,4-(3H,5H)-dione and β-dimethylamino-ethyl bromide.

EXAMPLE [12] 9

Using a procedure analogous to that described in Example 2, 1-(β-diethylamino-ethyl)-7-chloro-5-phenyl-1H-1,5-benzodiazepine-2,4-(3H,5H)-dione, m.p. 145°C, was prepared from 7-chloro-5-phenyl-1H-1,5-benzodiazepine-2,4-(3H,5H)-dione and β-diethylamino-ethyl bromide.

EXAMPLE [13] 10

Using a procedure analogous to that described in Example 2, 1-(ethoxycarbonyl-methyl)-7-chloro-5-phenyl-1H-1,5-benzodiazepine-2,4-(3H,5H)-dione, m.p. 159–160°C, of the formula

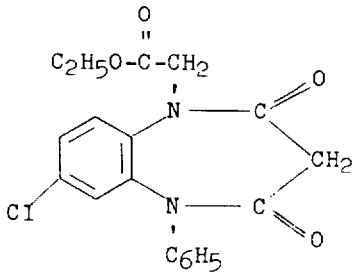

was prepared from 7-chloro-5-phenyl-1H-1,5-benzodiazepine-2,4-(3H,5H)-dione and ethoxycarbonyl-methyl bromide.

EXAMPLE [14] 11

Using a procedure analogous to that described in Example 2, 1-(γ-chloro-n-propyl)-7-chloro-5-phenyl)-1H-1,5-benzodiazepine-2,4-(3H,5H)-dione, m.p. 156–158°C, of the formula

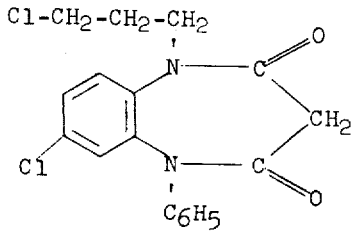

was prepared from 7-chloro-5-phenyl-1H-1,5-benzodiazepine-2,4-(3H,5H)-dione and 1,3-dichloro-propane.

EXAMPLE [15] 12

Using a procedure analogous to that described in Example 2, 1-(methoxycarbonyl-allyl)-7-chloro-5-phenyl-1H-1,5-benzodiazepine-2,4-(3H,5H)-dione, m.p. 172–174°C, of the formula

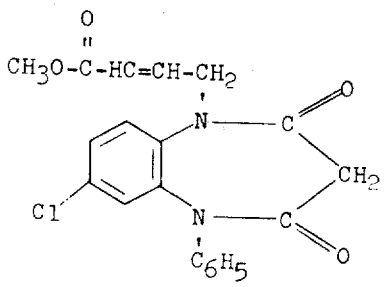

was prepared from 7-chloro-5-phenyl-1H-1,5-benzodiazepine-2,4-(3H,5H)-dione and methoxycarbonyl-allyl bromide.

EXAMPLE [16] 13

Using a procedure analogous to that described in Example 2, 1-(β-ethylmercapto-ethyl)-7-chloro-5-phenyl)-1H-1,5-benzodiazepine-2,4-(3H,5H)-dione, m.p. 129–131°C, of the formula

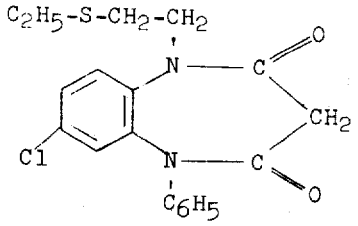

was prepared from 7-chloro-5-phenyl-1H-1,5-benzodiazepine-2,4-(3H,5H)-dione and β-ethylmercapto-ethyl bromide.

EXAMPLE [17] 14

Using a procedure analogous to that described in Example 2, 1-(γ-hydroxy-n-propyl)-5-phenyl-7-chloro-1H-1,5-benzodiazepine-2,4-(3H,5H)-dione, m.p. 211–213°C. was prepared from 5-phenyl-7-chloro-1H-1,5-benzodiazepine-2,4-(3H,5H)-dione and 3-chloro-propanol.

EXAMPLE [18] 15

Using a procedure analogous to that described in Example 2, 1-(γ-piperidino-n-propyl)-5-phenyl-7-chloro-1H-1,5-benzodiazepine-2,4-(3H,5H)-dione, m.p. 142–144°C, of the formula

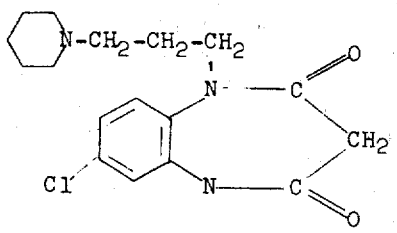

was prepared from 5-phenyl-7-chloro-1H-1,5-benzodiazepine-2,4-(3H,5H)-dione and piperidino-n-propyl bromide.

The compounds according to the present invention, that is, those embraced by formula I above, have useful pharmacodynamic properties. More particularly, they exhibit very effective psychosedative (tranquilizing) and anticonvulsive activities in warm-blooded animals, such as mice, rats and dogs, coupled with low toxicity.

Particularly effective are compounds of the formula I wherein $R_1$ is ω-hydroxy-alkyl, ω-alkoxy-alkyl or dialkylamino-alkyl, and especially 1-(β-hydroxy-ethyl)-5-phenyl-7-chloro-1H-1,5-benzodiazepine-2,4-(3H,5H)-dione, 1-(methoxy-methyl)-5-phenyl-7-chloro-1H-1,5-benzodiazepine-2,4-(3H,5H)-dione and 1-(β-methoxy-ethyl)-5-phenyl-7-chloro-1H-1,5-benzodiazepine-2,4-(3H,5H)-dione.

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0166 to 0.833 mgm/kg body weight, preferably 0.0833 to 0.42 mgm/kg, and the daily dose rate is from 0.166 to 2.5 mgm/kg.

The following examples illustrate a few dosage unit compositions comprising a compound of the instant invention as an active ingredient and represent the best mode contemplated of putting the invention to practical use. The parts are parts by weight unless otherwise specified.

EXAMPLE [19] *16*

Coated pills

The pill core composition was compounded from the following ingredients:

| | |
|---|---|
| 1-(β-hydroxy-ethyl)-5-phenyl-7-chloro-1H-1,5-benzodiazepine-2,4-(3H,5H)-dione | 10.0 parts |
| Lactose | 28.5 " |
| Corn starch | 15.0 " |
| Gelatin | 1.0 " |
| Magnesium stearate | 0.5 " |
| Total | 55.0 parts |

Compounding procedure:

The benzodiazepinedione compound was intimately admixed with the lactose and the corn starch, the mixture was moistened with an aqueous 10% solution of the gelatin, the moist mass was forced through a 1-mm-mesh screen, and the granulate obtained thereby was dried at 40°C and again passed through the screen. The dry granulate was admixed with the magnesium stearate, and the mixture was pressed into 55 mgm-pill cores, which were subsequently coated with a thin shell with the aid of an aqueous suspension of sugar, talcum, titanium dioxide and gum arabic, and the coated pills were polished with beeswax. One coated pill contained 10 mgm of the benzodiazepinedione compound and, when administered to a warm-blooded animal of about 60 kg body weight in need of such treatment, produced very good tranquilizing and anticonvulsive effects.

The same results were obtaned when the benzodiazepinedione compound in the above pill core composition was replaced by an equal amount of one of the following benzodiazepinediones:

a. 1-(γ-Hydroxy-n-propyl)-5-phenyl-7-chloro-1H-1,5-benzodiazepine-2,4-(3H,5H)-dione;
b. 1-(β-Methoxy-ethyl)-5-phenyl-7-chloro-1H-1,5-benzodiazepine-2,4-(3H,5H)-dione; or
c. 1-(Dimethylamino-ethyl)-5-phenyl-7-chloro-1H-1,5-benzodiazepine-2,4-(3H,5H)-dione.

EXAMPLE [20] *17*

Suppositories

The suppository composition was compounded from the following ingredients:

| | |
|---|---|
| 1-(γ-hydroxy-n-propyl)-5-phenyl-7-chloro-1H-1,5-benzodiazepine-2,4-(3H,5H)-dione | 10.0 parts |
| Cocoa butter | 1690.0 parts |
| Total | 1700.0 parts |

Compounding procedure:

The finely powdered benzodiazepinedione compound was stirred, with the aid of an immersion homogenizer, into the cocoa butter which had previously been melted and cooled to about 40°C. The homogenous mixture was then cooled to 35°C and was poured into cooled suppository molds, each holding 1700 mgm of the mixture. One suppository contained 10 mgm of the benzodiazepinedione compound and, when administered by the rectal route to a warm-blooded animal of about 60 kg body weight in need of such treatment, produced very good tranquilizing and anticonvulsive effects.

Analogous results were obtained when any one of the other benzodiazepinediones embraced by formula I was substituted for the particular benzodiazepinedione in Examples [19] *16* and [20] *17*. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

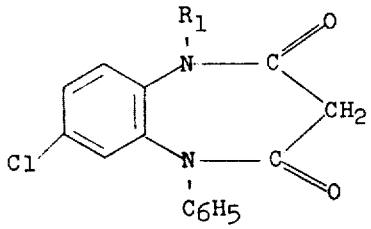

wherein $R_1$ is hydroxy-alkyl of 2 to 4 carbon atoms; haloalkyl of 2 to 4 carbon atoms; di(alkyl of 2 to 4 carbon atoms)amino-alkyl of 2 to 4 carbon atoms; γ-piperidino-propyl; alkoxy of 1 to 2 carbon atoms-alkyl of 1 to 4 carbon atoms; (alkoxy of 1 to 2 carbon atoms)carbonyl-alkyl of 1 to 4 carbon atoms; (alkyl of 1 to 2 carbon atoms)mercaptoalkyl of 1 to 4 carbon atoms; [straight or branched alkenyl of 3 to 5 carbon atoms;] (alkoxy of 1 to 2 carbon atoms)carbonyl-alkenyl of 2 to 4 carbon atoms; or halo-alkenyl of 2 to 4 carbon atoms.

2. A compound according to claim 1, wherein $R_1$ is ω-hydroxy-alkyl of 2 to 3 carbon atoms, γ-chloro-n-propyl, β-di(alkyl of 1 to 2 carbon atoms)amino-ethyl, γ-piperidino-n-propyl, γ-alkoxy of 1 to 2 carbon atoms-alkyl of 1 to 2 carbon atoms, ethoxycarbonyl-methyl, β-ethylmercapto-ethyl, [alkenyl of 3 to 5 carbon atoms,] γ-methoxycarbonyl-allyl or γ-chloro-allyl.

3. A compound according to claim 1, wherein $R_1$ is ω-hydroxy-alkyl of 2 to 3 carbon atoms, ω-alkoxy of 1 to 2 carbon atoms-alkyl of 1 to 2 carbon atoms or β-di(alkyl of 1 to 2 carbon atoms)amino-ethyl.

4. A compound according to claim 1, which is 1-(β-hydroxy-ethyl)-5-phenyl-7-chloro-1H-1,5benzodiazepine-2,4-(3H,5H)-dione.

5. A compound according to claim 1, which is 1-(β-methoxy-ethyl)-5-phenyl-7-chloro-1H-1,5-benzodiazepine-2,4-(3H,5H)-dione.

6. A compound according to claim 1, which is 1-methoxymethyl-5-phenyl-7-chloro-1H-1,5-benzodiazepine-2,4-(3H,5H)-dione.

7. A compound according to claim 1, which is 1-(γ-hydroxy-n-propyl)-5-phenyl-7-chloro-1H-1,5-benzodiazepine-2,4-(3H,5H)-dione.

8. A compound according to claim 1, which is 1-(β-dimethylamino-ethyl)-5-phenyl-7-chloro-1H-1,5-benzodiazepine2,4-(3H,5H)-dione.

* * * * *

UNITED STATES PATENT OFFICE

CERTIFICATE OF CORRECTION

Patent No. Re. 28,935 Dated August 17, 1976

Inventor(s) KARL-HEINZ WEBER, KARL ZEILE, PETER DANNEBERG ROLF GIESEMANN, KARL-HEINZ HAUPTMANN It is certified that error appears in the above-identified patent and that said Letters Patent are hereby corrected as shown below:

| | |
|---|---|
| Col. 1, Line 41 | After "atoms" -- ; or halo-alkenyl of 2 to 4 carbon atoms. -- should be added |
| Col. 4, Line 45 | That portion of the formula which reads "$H_3CO-CH_2-CH_2$" should read -- $HO-CH_2-CH_2$ -- |
| Col. 5, Line 5 | That portion of the formula which reads "$HO-CH_2-CH_2$" should read -- $H_3CO-CH_2-CH_2$ -- |
| Col. 12, Line 1 | "γ-alkoxy" should read -- ω-alkoxy -- |

Signed and Sealed this

Ninth Day of November 1976

[SEAL]

*Attest:*

RUTH C. MASON
*Attesting Officer*

C. MARSHALL DANN
*Commissioner of Patents and Trademarks*